United States Patent
Binder (10) Patent No.: US 11,981,888 B2
(45) Date of Patent: *May 14, 2024

(54) SYNTHESIS OF FURANS FROM SUGARS VIA KETO INTERMEDIATES

(71) Applicant: BP Corporation North America Inc., Houston, TX (US)

(72) Inventor: Joseph B. Binder, Haverford, PA (US)

(73) Assignee: BP Corporation North America Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/527,142

(22) Filed: Nov. 15, 2021

(65) Prior Publication Data

US 2022/0145238 A1  May 12, 2022

Related U.S. Application Data (63) Continuation of application No. 15/556,084, filed as application No. PCT/US2016/020621 on Mar. 3, 2016, now Pat. No. 11,193,106.

(60) Provisional application No. 62/128,767, filed on Mar. 5, 2015.

(51) Int. Cl.

| | | |
|---|---|---|
| C12N 1/14 | (2006.01) | |
| C07D 307/44 | (2006.01) | |
| C07D 307/48 | (2006.01) | |
| C07D 307/56 | (2006.01) | |
| C07H 19/01 | (2006.01) | |
| C12N 9/24 | (2006.01) | |
| C12R 1/685 | (2006.01) | |

(52) U.S. Cl.
CPC ........... *C12N 1/145* (2021.05); *C07D 307/44* (2013.01); *C07D 307/48* (2013.01); *C07D 307/56* (2013.01); *C07H 19/01* (2013.01); *C12N 9/24* (2013.01); *C12R 2001/685* (2021.05)

(58) Field of Classification Search
CPC ........ C12N 1/145; C12N 9/24; C07D 307/44; C07D 307/48; C07D 307/56; C07D 307/68; C07H 19/01; C12R 2001/685; C12P 17/04
See application file for complete search history.

(56) References Cited

U.S. PATENT DOCUMENTS

| | | | | |
|---|---|---|---|---|
| 11,193,106 | B2 * | 12/2021 | Binder | ..................... C12N 9/24 |
| 2014/0206047 | A1 * | 7/2014 | Kambourakis | ........... C12P 7/42 |
| | | | | 435/126 |

FOREIGN PATENT DOCUMENTS

| | | |
|---|---|---|
| CN | 10161331 | 9/2011 |
| EP | 0518136 | 5/1992 |
| WO | 2011/124639 | 10/2011 |
| WO | 2012/030860 | 3/2012 |
| WO | 2013/049711 | 4/2013 |
| WO | 2014/047510 | 3/2014 |
| WO | WO 2014047510 A1 * | 7/2014 |
| WO | 2014/182171 | 11/2014 |

OTHER PUBLICATIONS

Znad et al. Production of gluconic acid from glucose by Aspergillus niger: growth and non-growth conditions. Process Biochemistry 39 (2004): 1341-1345. (Year: 2004).*
Kim et al., 2006 "Catalytic Promiscuity in Dihydroxy-Acid Dehydratase from the Thermoacidophilic Archaeon Sulfolobus solfataricus," The Journal of Biochemistry, 139(3): 591-596.
Plantier-Royon et al., 1991 "Nouvelle Synthese de L'Acide 3-Desoxy-D-Erythro-2-Hexulosonique (Kdg). A Partir De La D-Glucono-1,5-Lactone Synthese Et Etude De RMN De Derives O-Methyles Du KDG," Journal of Carbohydrate Chemistry, 10(5): 787-811.
Znad et al., 2004 "Production of gluconic acid from glucose by Aspergillus niger: growth and non-growth conditions," Process Biochemistry, 39: 1341-1345.
International Search Report and Written Opinion for International Application No. PCT/US2016/020621, dated May 17, 2016.

* cited by examiner

*Primary Examiner* — Iqbal H Chowdhury
(74) *Attorney, Agent, or Firm* — Biospark Intellectual Property Law (57) ABSTRACT

The present invention provides a method of preparing a furan derivative comprising the steps of (a) converting a monosaccharide to provide a keto-intermediate product; and (b) dehydrating the keto-intermediate product to provide a furan derivative; wherein the keto-intermediate product is pre-disposed to forming keto-furanose tautomers in solution. The method may further comprise a step of oxidizing the furan derivative to provide a furandicarboxylic acid or a furandicarboxylic acid derivative.

16 Claims, 4 Drawing Sheets

SYNTHESIS OF FURANS FROM SUGARS VIA KETO INTERMEDIATES

CROSS-REFERENCE TO RELATED APPLICATIONS

This application is a continuation of U.S. application Ser. No. 15/556,084, which is a national stage application of international application no. PCT/US2016/020621, filed Mar. 3, 2016, the contents of which are incorporated by reference herein in their entireties. International application no. PCT/US2016/020621 claims the priority benefit of U.S. application No. 62/128,767, filed Mar. 5, 2015.

FIELD OF THE INVENTION

The present invention relates to a method of preparing a furan derivative via a keto-intermediate product. The method may further comprise a step of oxidizing the furan derivative to provide furandicarboxylic acid or a furandicarboxylic acid derivative.

BACKGROUND OF THE INVENTION

Five-carbon and six-carbon furans such as furfural and 5-hydroxymethylfurfural may be derived from renewable resources and are promising platform chemicals which may be used in a wide range of applications. For instance, 5-hydroxymethylfurfural may be oxidized into 2,5-furandicarboxylic acid, a component of polyesters resembling polyethylene terephthalate but with improved barrier properties. The challenge of producing furan compounds such as 5-hydroxymethylfurfural in high yield at low cost hinders such applications. 5-hydroxymethylfurfural is traditionally produced from fructose, yet fructose is not as common as other sugars like sucrose and glucose and the pathways are not efficient. Therefore, new routes to furans like 5-hydroxymethylfurfural are needed.

One of the problems with 5-hydroxymethylfurfural synthesis is that 5-hydroxymethylfurfural itself is not very stable and is difficult to isolate. Therefore routes to furans in which 5-hydroxymethylfurfural is not an isolated intermediate are advantageous.

Moreover, most routes to bio-based furans use fructose as an intermediate. Glucose is a more common and cheaper sugar, but glucose is either converted into fructose in situ or ex situ to make furans such as 5-hydroxymethylfurfural. Routes to furans which did not require fructose as an intermediate would be advantageous.

SUMMARY OF THE INVENTION

Therefore what is provided herein is a method of preparing a furan derivative comprising the steps of (a) converting a monosaccharide to provide a keto-intermediate product; and (b) dehydrating the keto-intermediate product to provide a furan derivative, wherein the keto-intermediate product is pre-disposed to forming keto-furanose tautomers in solution. The method may further comprise a step of oxidizing the furan derivative to provide a furandicarboxylic acid or a furandicarboxylic acid derivative. The furandicarboxylic acid derivative may be a furandicarboxylic acid ester.

DETAILED DESCRIPTION OF THE INVENTION

One of the reasons which makes fructose a key intermediate for production of bio-furans with 2,5-substituents is that fructose has a 2-keto functionality. This 2-keto functionality allows fructose to form keto-furanose tautomers in solution, and these keto-furanose tautomers are pre-disposed to dehydration into 2,5-disubstituted furans.

In contrast, glucose does not adopt any furanose forms, making it a poor precursor for furan formation. However, there are other sugars which can form furanose tautomers. In fact, sugars such as 2-keto-3-deoxygluconic acid, 2-keto-D-gluconate, 5-keto-D-gluconic acid, D-lyxo-5-hexosulose, and 3-deoxy-D-fructose adopt furanose forms at even higher fractions than fructose, and this pre-disposes them to dehydration into furans.

The invention takes this insight from the structure of fructose and applies it to non-fructose sugars. In effect, the invention converts other sugars into derivatives which have keto functionality like that of fructose and have a pre-disposition to form keto-furanose tautomers in solution.

As shown in

Table 1, NMR spectroscopy measurements show that fructose is present as more than 25% furanose form in water, and this fraction of furanose is even higher in other solvents such as DMSO. In contrast, glucose does not adopt any furanose forms, making it a poor precursor for furan formation. However, there are other sugars which can form furanose tautomers. In fact, sugars such as 2-keto-3-deoxygluconic acid, 2-keto-D-gluconate, 5-keto-D-gluconic acid, 3-deoxy-D-fructose, and D-lyxo-5-hexosulose adopt furanose forms at even higher fractions than fructose, and this pre-disposes them to dehydration into furans.

TABLE 1

Tautomeric Composition of Sugars in Solution

| Sugar | Temp. (° C.) | Solvent | keto | α-pyranose | β-pyranose | α furanose | β furanose | % furanose |
|---|---|---|---|---|---|---|---|---|
| D-Fructose | 20 | D$_2$O | 0.5 | 2.7 | 68.2 | 6.2 | 22.4 | 28.6 |
| D-glucose | 31 | D$_2$O |  | 38 | 62 |  |  | 0 |
| 2-keto-3-deoxy-D-gluconic acid (KDG) | 20 | D$_2$O | 0 | 11 | 49 | 23 | 17 | 40 |

TABLE 1-continued

Tautomeric Composition of Sugars in Solution

| Sugar | Temp. (° C.) | Solvent | keto | α-pyranose | β-pyranose | α furanose | β furanose | % furanose |
|---|---|---|---|---|---|---|---|---|
| D-arabino-2-hexulosonic acid (2-KG) | 20 | D$_2$O | | 73 | 0 | 16 | 11 | 73 |
| | 20 | DMSO | | 36 | 6 | 35 | 23 | 42 |
| | 20 | DMF | | 42 | 0 | 36 | 22 | 42 |
| Sodium D-xylo-5-hexulosonate (5-KG) | 20 | D$_2$O | 11 | | | 10 | 79 | 89 |
| 3-deoxy-D-fructose (3-DF) | 22 | D$_2$O | 7.5 | 5 | 52.5 | 20 | 15 | 35 |
| D-lyxo-5-hexosulose | | D$_2$O | 8 | 0 | 10 | 14 | 52 | 66 |

2-keto-3-deoxygluconic acid, 5-keto-D-gluconic acid, and 2-keto-D-gluconate are the most common 2- or 5-keto sugars which are known to prefer furanose tautomeric forms. 4-deoxy-5-ketoglucaric acid is another example of a 5-keto sugar which occurs naturally. Several keto sugars which prefer furanose forms have been reported in the literature, including 3-deoxy-D-fructose, D-lyxo-5-hexulosonic acid, D-lyxo-5-hexosulose, and 4-deoxy-5-ketogalactaric acid. However, there are probably other 2- and 5-keto sugars which prefer furanose tautomeric forms but are not known.

Many of the 2-keto or 5-keto derivatives may be produced by enzymatic chemistry in high selectivity, including enzymes from the modified Entner-Doudoroff pathway. While it is most likely that the reaction pathway would be practiced with glucose, analogous pathways may be used with other C-6 sugars such as galactose and mannose.

Other dehydration products derived from glucose, sorbitol, or glucose oxidation products which have the 2-keto or 5-keto functionality for dehydration into furans include, but are not limited to, the following:

From glucose:

2-keto-3-deoxy-D-glucose 6-hydroxy-2,5-dioxohexanal

4-deoxy-5-keto-D-glucose

From sorbitol:

3-deoxy-D-erythro-hexulose (3-DF)

-continued 1,6-dihydroxy-2,5-diketohexane

From single oxidation products:

5-keto-D-glucose 2-keto-D-glucose 4-deoxy-5-keto-D-gluconic acid 2-keto-3-deoxy-D-gluconic acid

From double oxidation products:

4-Deoxy-5-keto-D-fructuronic acid

3-Deoxy-5-keto-D-fructuronic acid (3S)-2,5-dioxo-3-hydroxyhexanedial

From treble oxidation products:

(3S)-3-hydroxy-2,5,6-trioxohexanoic acid (4S)-4-hydroxy-2,5,6-trioxohexanoic acid (3S,4S)-3,4-dihydroxy-2,5-dioxohexanedial Alternatively, there are some 2- and 5-keto sugars which do not prefer furanose tautomeric forms, including L-sorbose, 5-ketoglucose, L-xylo-2-hexulosonic acid, D-glucosone, D-allosone, D-galactosone, and 3-deoxy-D-glucosone. These sugars would not be preferred candidates for dehydration to furans.

Now therefore, what is provided in a first embodiment is a method of preparing a furan derivative comprising the steps of (a) converting a monosaccharide to provide a keto-intermediate product, and (b) dehydrating the keto-intermediate product to provide a furan derivative, wherein the keto-intermediate product is pre-disposed to forming keto-furanose tautomers in solution. The method may further comprise a step of oxidizing the furan derivative to provide a furandicarboxylic acid or a furandicarboxylic acid derivative such as, but not limited thereto, a furandicarboxylic acid ester.

In one embodiment, the keto-intermediate product is pre-disposed to forming at least 30% keto-furanose tautomers in solution such as, for example but not limited thereto, water at a temperature of about 25° C.

In one embodiment, the monosaccharide is an aldohexose selected from a group consisting of allose, altrose, glucose, mannose, gulose, idose, galactose, and talose. In another embodiment, the monosaccharide is an aldohexose selected from a group consisting of D-allose, D-altrose, D-glucose, D-mannose, D-gulose, D-idose, D-galactose, and D-talose.

In one embodiment, the furan derivative is 5-hydroxymethyl-2-furoic acid.

In one embodiment the, keto-intermediate product is a 2-keto derivative of the monosaccharide. In another embodiment, the keto-intermediate product is a 5-keto derivative of the monosaccharide. In yet another embodiment, the keto-intermediate product is selected from the group consisting of 3-deoxy-D-fructose, D-lyso-5-hexulosonic acid and 4-deoxy-5-ketogalactactaric acid or any combination thereof.

In one embodiment, dehydration of the keto-intermediate product occurs by acid catalysis.

In one embodiment, step (a) of the method comprises oxidation of the monosaccharide to provide an oxidized-product followed by dehydration of the oxidized product to provide a keto-intermediate product, wherein the oxidized product is gluconic acid and wherein the keto-intermediate product is 2-keto-3-deoxygluconic acid.

In one embodiment, oxidation of the monosaccharide occurs microbially. In another embodiment, oxidation of the monosaccharide occurs enzymatically.

In one embodiment, dehydration of the oxidized product comprises contacting the oxidized product with an enzyme to provide keto-intermediate product, wherein the enzyme is selected from the group consisting of Galactonate dehydratases having the classification E.C. 4.2.1.6, Altronate dehydratases having the classification E.C. 4.2.1.7, Mannonate dehydratases having the classification E.C. 4.2.1.8, Dihydroxyacid dehydratases having the classification E.C. 4.2.1.9, Gluconate dehydratases having the classification E.C. 4.2.1.39, Glucarate dehydratases having the classification E.C. 4.2.1.40, Galactarate dehydratases having the classification E.C. 4.2.1.42, D-Fuconate dehydratases having the classification E.C. 4.2.1.67, L-Fuconate dehydratases having the classification E.C. 4.2.1.68, Xylonate dehydratases having the classification E.C. 4.2.1.82, Gluconate/galactonate dehydratases having the classification E.C. 4.2.1.140, and L-Galactonate dehydratases having the classification E.C. 4.2.1.146. More specifically, the enzyme is selected from the group consisting of gluconate dehydratase and dihydroxyacid dehydratase or a combination thereof.

Figure 1:
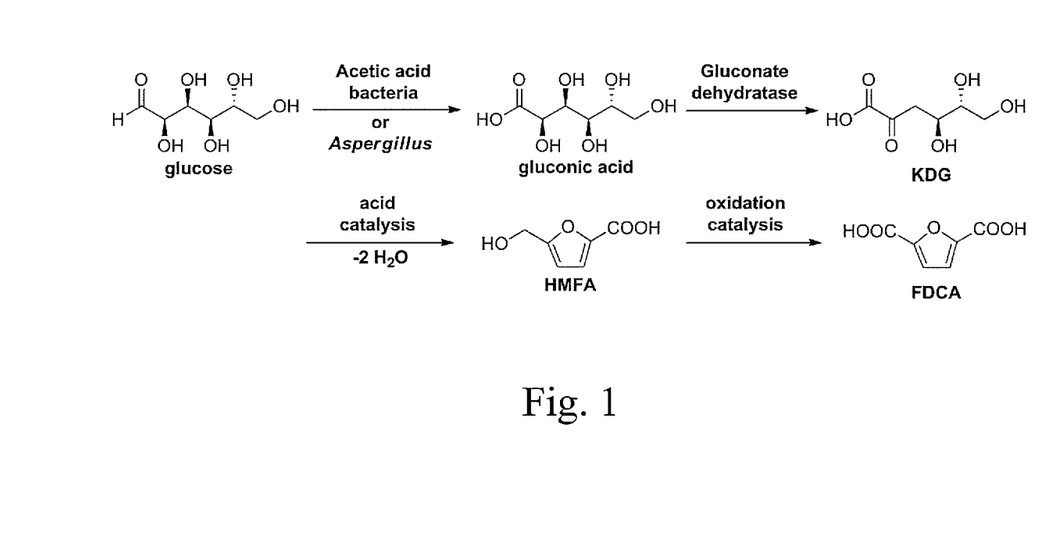
FIG. 1 shows the conversion of glucose to furandicarboxylic acid through 2-keto-3-deoxygluconic acid as a keto-sugar intermediate.

FIG. 1 illustrates a possible pathway of the invention utilizing a keto intermediate and its dehydration into a furan. Glucose can be oxidized microbially or enzymatically into gluconic acid. Gluconic acid can be dehydrated by gluconate dehydratase enzymes or dihydroxyacid dehydratase enzymes to form 2-keto-3-deoxygluconic acid, which is a 2-keto sugar which adopts furanose tautomeric forms. Consequently, 2-keto-3-deoxygluconic acid may be dehydrated by acid catalysis into 5-hydroxymethyl-2-furoic acid. 5-hydroxymethyl-2-furoic acid may be oxidized into furandicarboxylic acid using a variety of catalysts for oxidation of aldehydes to acids using a variety of oxidation systems. For example, 5-hydroxymethyl-2-furoic acid may be contacted with an oxygen source, acetic acid solvent, cobalt and manganese oxidation catalyst, a bromine source, at a temperature in the range of about 50° C. to about 200° C., and a pressure in the range of about 1 bar to about 100 bar for a period of time from about 1 minutes to about 10 hours to provide furandicarboxylic acid.

In one embodiment, step (a) of the method comprises oxidation of the monosaccharide to provide a keto-intermediate product such as, for example but not limited thereto, 5-ketogluconic acid, and step (b) of the method comprises dehydrating the keto-intermediate product to provide a furan derivative such as, for example but not limited thereto, 5-formyl-2-furoic acid.

Figure 2:
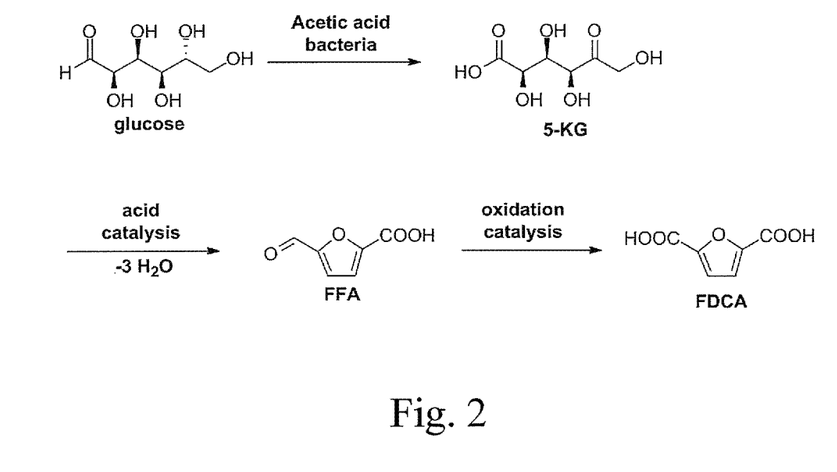
FIG. 2 shows the conversion of glucose to furandicarboxylic acid through 5-keto-D-gluconic acid as a keto-sugar intermediate.

FIG. 2 illustrates a possible pathway of the invention utilizing a keto intermediate and its dehydration into a furan. Glucose can be oxidized microbially into 5-keto-D-gluconic acid. This acid is a 5-keto sugar which adopts furanose tautomeric forms. Consequently, 5-keto-D-gluconic acid may be dehydrated by acid catalysis into 5-formyl-2-furoic acid. 5-formyl-2-furoic acid may be oxidized into furandicarboxylic acid using a variety of catalysts for oxidation of aldehydes to acids using a variety of oxidation systems. For example, 5-formyl-2-furoic acid may be contacted with an oxygen source, acetic acid solvent, cobalt and manganese oxidation catalyst, a bromine source, at a temperature in the range of about 50° C. to about 200° C., and a pressure in the range of about 1 bar to about 100 bar for a period of time from about 1 minutes to about 10 hours to provide furandicarboxylic acid.

In one embodiment, step (a) of the method comprises hydrogenation of the monosaccharide to provide a reduced-product followed by dehydration of the reduced product to provide a keto-intermediate product.

Figure 3:
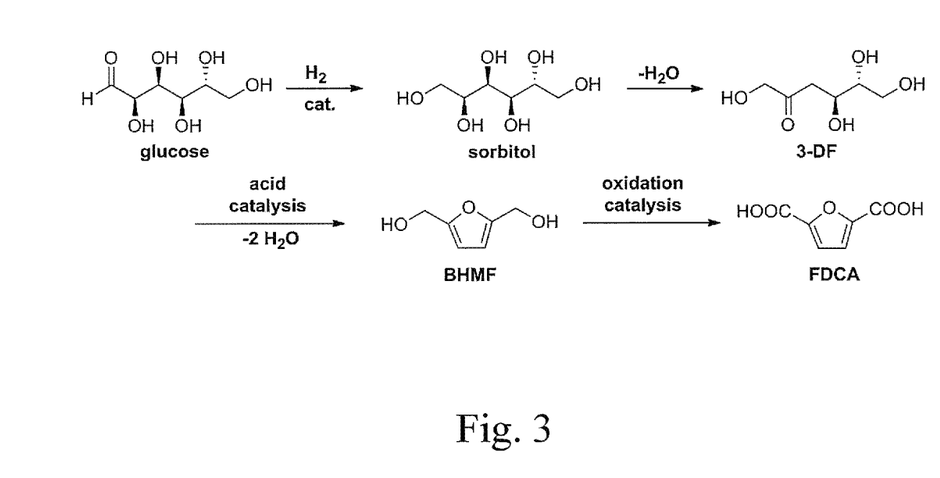
FIG. 3 shows the conversion of glucose to furandicarboxylic acid through 3-deoxy-D-fructose as a keto-sugar intermediate.
Figure 4:
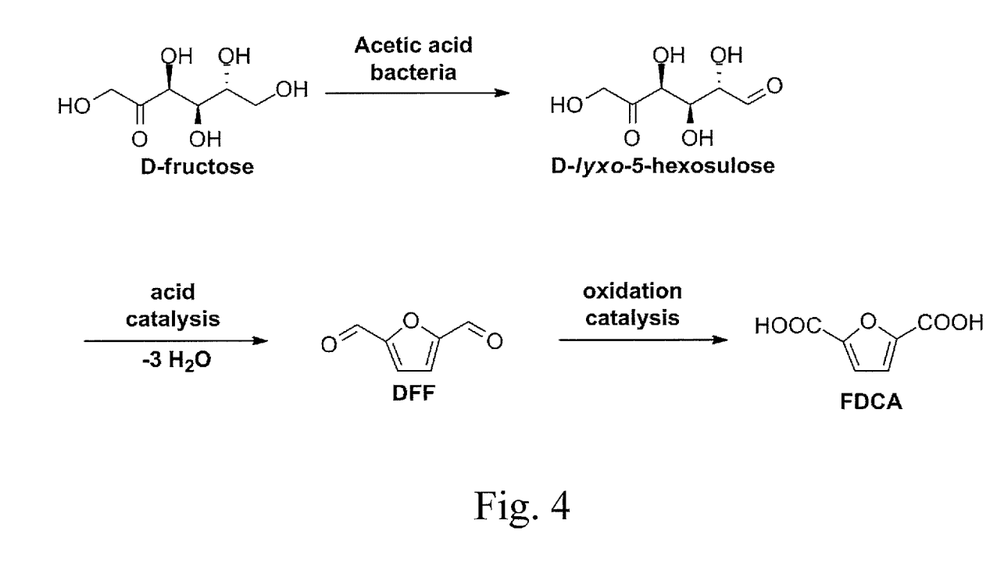
FIG. 4 shows the conversion of fructose to furandicarboxylic acid through D-lyxo-5-hexosulose as a keto-sugar intermediate.

FIG. 3 illustrates a possible pathway of the invention utilizing a keto intermediate and its dehydration into a furan. Glucose can be hydrogenated catalytically into sorbitol. If a new enzymatic activity may be found to selectively dehydrate sorbitol to 3-deoxy-D-fructose, then it can be converted into this keto-sugar. This 3-deoxy-D-fructose may be dehydrated by acid catalysis into 2,5-bis(hydroxymethyl) furan. 2,5-bis(hydroxymethyl)furan may be oxidized into furandicarboxylic acid using a variety of catalysts for oxidation of aldehydes to acids using a variety of oxidation systems. For example, 2,5-bis(hydroxymethyl)furan may be contacted with an oxygen source, acetic acid solvent, cobalt and manganese oxidation catalyst, a bromine source, at a temperature in the range of about 50° C. to about 200° C., and a pressure in the range of about 1 bar to about 100 bar for a period of time from about 1 minutes to about 10 hours to provide furandicarboxylic acid.

In a second embodiment, what is provided is a method of preparing a furan derivative comprising the steps of (a) oxidizing a monosaccharide to provide a keto-intermediate product, and (b) dehydrating the keto-intermediate product to provide a furan derivative; wherein the keto-intermediate product is pre-disposed to forming keto-furanose tautomers in solution. In one embodiment, the keto-intermediate product is pre-disposed to forming at least 30% keto-furanose tautomers in solution such as, for example but not limited thereto, water at a temperature of about 25° C.

In a third embodiment, what is provided is a method of preparing a furan derivative comprising the steps of (a) oxidizing glucose to provide 5-ketogluconic acid, and (b) dehydrating 5-ketogluconic acid to provide 5-formyl-2-furoic acid, wherein 5-ketogluconic acid is pre-disposed to forming keto-furanose tautomers in solution. In one embodiment, the 5-ketogluconic acid is pre-disposed to forming at least 30% keto-furanose tautomers in solution such as, for example but not limited thereto, water at a temperature of about 25° C.

In a fourth embodiment, what is provided is a method of preparing a furan derivative comprising the steps of (a) oxidizing a monosaccharide to provide an oxidation product, (b) dehydrating the oxidation product to provide a keto-intermediate product, and (c) dehydrating the keto-intermediate product to provide a furan derivative, wherein the keto-intermediate product is pre-disposed to forming keto-furanose tautomers in solution. In one embodiment, the keto-intermediate product is pre-disposed to forming at least 30% keto-furanose tautomers in solution such as, for example but not limited thereto, water at a temperature of about 25° C.

In a fifth embodiment, what is provided is a method of preparing a furan derivative comprising the steps of (a) oxidizing glucose to provide gluconic acid, (b) dehydrating gluconic acid to provide 2-keto-3-deoxygluconic acid, and (c) dehydrating 2-keto-3-deoxygluconic acid to provide 5-hydroxymethyl-2-furoic acid, wherein 2-keto-3-deoxygluconic acid is pre-disposed to forming keto-furanose tautomers in solution. In one embodiment, the 2-keto-3-deoxygluconic acid is pre-disposed to forming at least 30% keto-furanose tautomers in solution such as, for example but not limited thereto, water at a temperature of about 25° C.

In a sixth embodiment what is provided is a method of preparing 2,5-furandicarboxylic acid comprising the steps of (a) oxidizing glucose to provide gluconic acid, (b) dehydrating gluconic acid to provide 2-keto-3-deoxygluconic acid, (c) dehydrating 2-keto-3-deoxygluconic acid to provide 5-hydroxymethyl-2-furoic acid, and (d) oxidizing 5-hydroxymethyl-2-furoic acid to provide 2,5-furandicarboxylic acid, wherein 2-keto-3-deoxygluconic acid is pre-disposed to forming keto-furanose tautomers in solution. In one embodiment, the 2-keto-3-deoxygluconic acid is pre-disposed to forming at least 30% keto-furanose tautomers in solution such as, for example but not limited thereto, water at a temperature of about 25° C.

In one embodiment, the glucose of step (a) is contacted with at least one an enzyme to form gluconic acid, wherein the enzyme is selected from the group consisting of glucose oxidase and glucose dehydrogenase or a combination thereof.

In another embodiment, the glucose of step (a) is oxidized by a microbe to produce gluconic acid, wherein the microbe is selected from the group consisting of *Pseudomonas, Acetobacter, Zynomonas, Gluconobacter, Azospirillum, Aspergillus, Penicillium, Gliocladiun, Scopulariopsis, Gonatobotrys, Endomycopsis, Aureobasidium, Tricholoma,* and *Gluconacetobacter*. More specifically, the microbe is selected from the group consisting of *Pseudomonas ovalis, Pseudomonas savastanoi, Acetobacter methanolicus, Zymomonas mobilis, Acetobacter diazotrophicus, Gluconobacter oxydans, Gluconobacter suboxydans, Azospirillum brasiliense, Aspergillus niger, Penicillium fimiculosun, Penicillium glaucum, Penicillium variabile, Penicillium amagasakiense, Aureobasidium pullulans, Tricholoma robustum, Pseudomonas fluorescens, Gluconobacter cerinus, Gluconacetobacter diazotrophicus, Acetobacter aceti, Acetobacter pasteurianus, Acetobacter tropicalis,* and *Gluconacetobacter xylinus.*

In one embodiment, the gluconic acid of step (b) is contacted with at least one enzyme to form 2-keto-3-deoxygluconic acid, wherein the enzyme is selected from the group consisting of Galactonate dehydratases having the classification E.C. 4.2.1.6, Altronate dehydratases having the classification E.C. 4.2.1.7, Mannonate dehydratases having the classification E.C. 4.2.1.8, Dihydroxyacid dehydratases having the classification E.C. 4.2.1.9, Gluconate dehydratases having the classification E.C. 4.2.1.39, Glucarate dehydratases having the classification E.C. 4.2.1.40, Galactarate dehydratases having the classification E.C. 4.2.1.42, D-Fuconate dehydratases having the classification E.C. 4.2.1.67, L-Fuconate dehydratases having the classification E.C. 4.2.1.68, Xylonate dehydratases having the classification E.C. 4.2.1.82, Gluconate/galactonate dehydratases having the classification E.C. 4.2.1.140, and L-Galactonate dehydratases having the classification E.C. 4.2.1.146. More specifically, the enzyme is selected from the group consisting of gluconate dehydratase and dihydroxyacid dehydratase.

In one embodiment, the 2-keto-3-deoxygluconic acid of step (c) undergoes acid catalysed dehydration by contacting the 2-keto-3-deoxygluconic acid with an acid to provide 5-hydroxymethyl-2-furoic acid, wherein the acid is selected from the group consisting of acetic acid, sulphuric acid, trifluoroacetic acid, hydrobromic acid, hydrochloric acid, and hydroiodic acid or any combination thereof. In one embodiment, the 2-keto-3-deoxygluconic acid in step (c) is subjected to acid catalysed dehydration by contacting the 2-keto-3-deoxygluconic acid with an acid and heated to a temperature in the range of about 10° C. to about 200° C. for a period of time of about 5 minutes to about 10 hours to provide 5-hydroxymethyl-2-furoic acid. In one embodiment, the acid is selected from the group consisting of acetic acid, sulphuric acid, trifluoroacetic acid, hydrobromic acid, hydrochloric acid, and hydroiodic acid or any combination thereof.

In one embodiment, the 5-hydroxymethyl-2-furoic acid of step (d) is oxidized to 2,5-furandicarboxylic acid by contacting the 5-hydroxymethyl-2-furoic acid with an oxygen source, acetic acid solvent, cobalt and manganese oxidation catalyst, a bromine source, at a temperature in the range of about 50° C. to about 200° C., and a pressure in the range of about 1 bar to about 100 bar for a period of time from about 1 minutes to about 10 hours.

In a seventh embodiment, what is provided is a method of preparing a furan derivative comprising the steps of (a) hydrogenating a monosaccharide to provide a reduced-product, (b) dehydrating the reduced-product to provide a keto-intermediate product, and (c) dehydrating the keto-intermediate product to provide a furan derivative, wherein the keto-intermediate product is pre-disposed to forming keto-furanose tautomers in solution. In one embodiment, the keto-intermediate product is pre-disposed to forming at least 30% keto-furanose tautomers in solution such as, for example but not limited thereto, water at a temperature of about 25° C.

In an eighth embodiment, what is provided is a method of preparing a furan derivative comprising the steps of (a) hydrogenating glucose to provide sorbitol, (b) dehydrating sorbitol to provide 3-deoxy-D-fructose, and (c) dehydrating 3-deoxy-D-fructose to provide 2,5-bis(hydroxymethyl) furan, wherein 3-deoxy-D-fructose is pre-disposed to forming keto-furanose tautomers in solution. In one embodiment, the 3-deoxy-D-fructose is pre-disposed to forming at least 30% keto-furanose tautomers in solution such as, for example but not limited thereto, water at a temperature of about 25° C.

In a ninth embodiment, what is provided is a method of preparing 2,5-furandicarboxylic acid comprising the steps of (a) hydrogenating glucose to provide sorbitol, (b) dehydrating sorbitol to provide 3-deoxy-D-fructose, (c) dehydrating 3-deoxy-D-fructose to provide 2,5-bis(hydroxymethyl) furan, and (d) oxidizing 2,5-bis(hydroxymethyl)furan to provide 2,5-furandicarboxylic acid, wherein 3-deoxy-D-fructose is pre-disposed to forming keto-furanose tautomers in solution. In one embodiment, the 3-deoxy-D-fructose is pre-disposed to forming at least 30% keto-furanose tautomers in solution such as, for example but not limited thereto, water at a temperature of about 25° C.

In a tenth embodiment, what is provided is a method of preparing a furan derivative comprising the steps of, (a) oxidizing fructose to provide D-lyxo-5-hexosulose, and (b) dehydrating D-lyxo-5-hexosulose to provide 2,5-diformyl-furan, wherein the D-lyxo-5-hexosulose is pre-disposed to forming keto-furanose tautomers in solution.

In one embodiment, the method further comprises the step of oxidizing 2,5-diformylfuran to provide 2,5-furandicarboxylic acid. For example, 2,5-diformylfuran may be contacted with an oxygen source, acetic acid solvent, cobalt and manganese oxidation catalyst, a bromine source, at a temperature in the range of about 50° C. to about 200° C., and a pressure in the range of about 1 bar to about 100 bar for a period of time from about 1 minutes to about 10 hours to provide furandicarboxylic acid.

In one embodiment, the keto-intermediate product is pre-disposed to forming at least 30% keto-furanose tautomers in solution such as, for example, but not limited thereto, water at a temperature of about 25° C.

EXAMPLES

Reagents 2-keto-3-deoxygluconic acid lithium salt hydrate, potassium 5-keto-D-gluconate, calcium 2-keto-D-gluconate hemihydrate, hydrogen bromide in acetic acid (33 wt %, HBr/HOAc), Hydrogen bromide in water (48 wt %, HBr), trifluoroacetic acid (TFA), acetic anhydride ($Ac_2O$), acetic acid, sulfuric acid (98% in water, $H_2SO_4$), and hydroiodic acid (57% in water, HI) were obtained from Sigma-Aldrich.

Example 1: Oxidation of Glucose into 5-Keto-D-Gluconic Acid

Glucose (20 g), polypeptone (2 g), and yeast extract (1 g) are mixed in 1 L of deionized water, and this medium is placed in a fermentation tank. The tank is inoculated with a culture of *Gluconobacter* suboxydans IFO 12528 and agitated and aerated at 30° C. for 170 hours with pH maintained at pH 3.5 by controlled addition of sodium hydroxide. During the fermentation, glucose is converted to sodium 5-ketogluconate with traces of sodium gluconate and sodium 2-ketogluconate.

Example 2: Oxidation of Glucose into 2-Keto-D-Gluconate

Glucose (100 g), corn steep liquor (5 g), urea (2 g), $MgSO_4$ heptahydrate (0.25 g), $KH_2PO_4$ (0.6 g), and $CaCO_3$ (27 g) are mixed in 1 L of deionized water, and this medium is placed in a fermentation tank. The tank is inoculated with a culture of *Pseudomonas fluorescens*, and agitated and aerated at 25° C. for 43 hours. During the fermentation, glucose is converted to calcium 2-ketogluconate.

Example 3: Oxidation of Glucose into Gluconate

Glucose (100 g) and yeast extract (10 g) are mixed in 1 L of deionized water, and this medium is divided amongst several shake flasks. Each flask containing medium is inoculated with a culture of *Gluconobacter oxydans*, and incubated at 32° C. for 8 hours in a shaker with good agitation for medium aeration. During the fermentation, glucose is converted to gluconate and gluconic acid.

Example 4: Dehydration of Gluconate into 2-Keto-3-Deoxygluconic Acid

The dihydroxyacid dehydratase from *Sulfolobus solfataricus* (Kim, S; Lee, S. B. "Catalytic Promiscuity in Dihydroxy-Acid Dehydratase from the Thermoacidophilic Archaeon *Sulfolobus solfataricus*." *Journal of Biochemistry*, 2006, 139, 591-596) was expressed in *E. coli*. The gene was synthesized, cloned into a vector, and transformed into *E. coli*. Transformed *E. coli* were grown on a shake flask scale to express the heterologous dihydroxyacid dehydratase protein. On completion of the fermentation, protein was extracted using a detergent extraction reagent and clarified protein extracts were produced. Gluconate dehydration reactions were performed by combining the clarified cell extract in a 1:1 volume ratio with 50 mM Tris HCl buffer containing 40 mM sodium gluconate (measured pH 8.35). These were incubated at 60° C. for 24.75 hours and analyzed by liquid chromatography for conversion of gluconate. Nearly all of the gluconate was converted to a new product. For positive identification of the 2-keto-3-deoxygluconic acid product, proton NMR was used. Comparison of the spectra of the enzymatic reaction samples show that gluconate has disappeared from the reaction mixture and new peaks corresponding to the reported spectrum of 2-keto-3-deoxygluconic acid have appeared (reported spectrum from Plantier-Royon, R.; Cardona, F.; Anker, D.; Condemine, G.; Nasser, W.; Robert-Baudouy, J. Nouvelle Synthese de L'Acide 3-Desoxy-D-Erythro-2-Hexulosonique. *J. Carbohydrate Chem.* 1991, 10, 787-811).

Example 5: Hydrogenation of Glucose into Sorbitol

Glucose is dissolved in water to produce a 40 wt % glucose solution, and the solution is adjusted to pH 8 using sodium hydroxide. The glucose solution is contacted with hydrogen gas at a hydrogen partial pressure of 2000 psig in the presence of Raney nickel catalyst at a temperature of 140° C. Under these conditions, glucose is converted to sorbitol in near quantitative yield.

Example 6: Dehydration of Sorbitol into 3-Deoxyfructose

Sorbitol is dissolved in 50 mM Tris HCl buffer to which a clarified cell extract containing dehydratase enzyme of class 4.2.1 is added. This mixture is incubated at 30° C. for 24 hours. Sorbitol is converted into 3-deoxyfructose.

Examples 7-18: Dehydration of 2-Keto-3-Deoxygluconic Acid into 5-Hydroxymethyl-2-Furoic Acid 2-keto-3-deoxygluconic acid was dissolved in water and acetic acid by placing 8.45 mg of 2-keto-3-deoxygluconic acid in a very small sample vial. To this was added 120 ul of water and 120 ul of acetic acid, and this was mixed to dissolve the 2-keto-3-deoxygluconic acid. This stock solution was used for each reaction according to Table 2. In each case, 20 ul of the 2-keto-3-deoxygluconic acid solution was added first to a vial along with a mini stir bar. The remaining reagents were added in the order shown in Table 2 (left to right) and mixed by stirring on a stirplate. Each vial was capped and heated to 60° C. with stirring. After the reaction time, the vial contents were cooled and analyzed for 5-hydroxymethyl-2-furoic acid by HPLC.

TABLE 2

Dehydration of 2-keto-3-deoxygluconic acid and yield of 5-hydroxymethyl-2-furoic acid

| # | $Ac_2O$ (ul) | Acetic (ul) | HBr/HOAc (ul) | $H_2O$ (ul) | Acid (ul) | Time (h) | Yield (mol %) |
|---|---|---|---|---|---|---|---|
| 7 | — | 365 | 375 | — | — | 4 | 12 |
| 8 | — | — | 740 | — | — | 4 | 7 |
| 9 | 405 | 299 | — | — | $H_2SO_4$, 36 | 4 | <5 |
| 10 | 365 | — | 375 | — | — | 4 | 6 |
| 11 | 364 | 263 | 113 | — | — | 4 | 6 |
| 12 | — | — | 675 | 65 | — | 4 | <5 |
| 13 | — | 337 | 338 | 65 | — | 4 | 10 |
| 14 | — | — | — | — | TFA, 740 | 4 | 45 |
| 15 | | | 683 | | TFA, 57 | 1 | 21 |
| 16 | | | 700 | | $H_2SO_4$, 40 | 1 | 15 |
| 17 | | | 655 | | HBr, 85 | 1 | 9 |
| 18 | | | 641 | | HI, 99 | 1 | <5 |

Examples 19-39: Dehydration of 5-keto-D-gluconic acid into 5-hydroxymethyl-2-furoic acid and 5-formyl-2-furoic acid Potassium 5-keto-D-gluconate (70 mg) was placed in a vial along with a mini stirbar. The other reagents in Table 3 were added to the vial in order from left to right and mixed by stirring on a stirplate. Each vial was capped and heated to the reaction temperature with stirring. After the reaction time, the vial contents were cooled and analyzed for furans by HPLC.

TABLE 3

Dehydration of 5-keto-D-gluconic acid into 5-hydroxymethyl-2-furoic acid (HMFA) and 5-formyl-2-furoic acid (FFA)

| # | 5-KG (mg) | LiBr (mg) | $H_2O$ (ul) | $Ac_2O$ (ul) | Acetic (ul) | Acetic/HBr (ul) | Other acid (ul) | Temp. (° C.) | Time (h) | HMFA % | FFA % |
|---|---|---|---|---|---|---|---|---|---|---|---|
| 19 | 70 | | 242 | | | 2700 | | 100 | 2 | 0.04 | |
| 20 | 70 | | | | 1500 | | 1500, $H_2SO_4$ | 100 | 2 | | |
| 21 | 70 | | | | 1500 | | 1500, MSA | 100 | 2 | | |
| 22 | 70 | | | 1430 | 1430 | — | 142, $H_2SO_4$ | 100 | 2 | | 0.7 |
| 23 | 70 | | | | | | 3000, 48% HBr | 100 | 2 | | |
| 24 | 70 | | 242 | | | | 2700, $H_2SO_4$ | 100 | 2 | | |
| 25 | 70 | | | | | | 3000, HCl | 100 | 2 | | |
| 26 | 70 | | | | | | 3000, TFA | 100 | 2 | | 0.2 |
| 27 | 70 | | 2700 | | | | 230, TFA | 100 | 2 | | |
| 28 | 140 | 2002 | 446 | | | | 1260, 48% HBr | 100 | 2 | | |
| 29 | 70 | | 242 | | | 2700 | | 60 | 4 | 6.9 | 0.03 |
| 30 | 70 | | | | 1500 | | 1500, $H_2SO_4$ | 60 | 4 | | 0.01 |
| 31 | 70 | | | | 1500 | | 1500, MSA | 60 | 4 | | 0.04 |
| 32 | 70 | | | 1430 | 1430 | — | 142, $H_2SO_4$ | 60 | 4 | | 0.75 |
| 33 | 70 | | | | | | 3000, 48% HBr | 60 | 4 | | 3.42 |
| 34 | 70 | | 242 | | | | 2700, $H_2SO_4$ | 60 | 4 | | 0.20 |
| 35 | 70 | | | | | | 3000, HCl | 60 | 4 | | 0.96 |

TABLE 3-continued

Dehydration of 5-keto-D-gluconic acid into 5-hydroxymethyl-2-furoic acid (HMFA) and 5-formyl-2-furoic acid (FFA)

| # | 5-KG (mg) | LiBr (mg) | H$_2$O (ul) | Ac$_2$O (ul) | Acetic (ul) | Acetic/HBr (ul) | Other acid (ul) | Temp. (° C.) | Time (h) | HMFA % | FFA % |
|---|---|---|---|---|---|---|---|---|---|---|---|
| 36 | 70 | | | | | | 3000, TFA | 60 | 4 | | |
| 37 | 70 | | | | | | 230, TFA | 60 | 4 | | 0.21 |
| 38 | 140 | 2002 | 2700 446 | | | | 1260, 48% HBr | 60 | 4 | | |
| 39 | 70 | | | | 3000 | | | 100 | 2 | | 1.7 |

Note:
Acetic acid/HBr refers to 33 wt % HBr in acetic acid. H$_2$SO$_4$ refers to 98% sulfuric acid. TFA is trifluoro acetic acid. Ac$_2$O is acetic anhydride. HCl is 37% concentrated hydrochloric acid. 48% HBr is 48% hydrobromic acid in water. MSA is methanesulfonic acid.

Examples 40-43: Dehydration of 2-keto-D-gluconate into 5-hydroxymethyl-2-furoic acid and 5-formyl-2-furoic acid Calcium 2-keto-D-gluconate hemihydrate (64 mg) was placed in a vial along with a mini stir bar. The other reagents in Table 4 were added to the vial in order from left to right, and mixed by stirring on a stirplate. Each vial was capped and heated to the reaction temperature with stirring. After the reaction time, the vial contents were cooled and analyzed for furans by HPLC.

TABLE 4

Dehydration of 2-keto-D-gluconate into 5-hydroxymethyl-2-furoic acid (HMFA) and 5-formyl-2-furoic acid (FFA)

| # | 2-KG (mg) | LiBr (mg) | H$_2$O (ul) | Ac$_2$O (ul) | Acetic (ul) | Acetic/HBr (ul) | Other acid (ul) | Temp. (° C.) | Time (h) | HMFA % | FFA % |
|---|---|---|---|---|---|---|---|---|---|---|---|
| 40 | 70 | | | | 3000 | | | 100 | 2 | 0.19 | 0.19 |
| 41 | 70 | | | | 3000 | | 58, H$_2$SO$_4$ | 100 | 2 | | 0.13 |
| 42 | 70 | | 242 | | | 2700 | | 60 | 4 | 18.9 | |
| 43 | 70 | | | | | | 3000, HCl | 60 | 4 | | 0.81 |

Note:
Acetic acid/HBr refers to 33 wt % HBr in acetic acid. H$_2$SO$_4$ refers to 98% sulfuric acid. HCl is 37% concentrated aqueous hydrochloric acid.

Examples 44-55: Dehydration of 3-Deoxyfructose into 2,5-bis(hydroxymethyl)furan 3-deoxy-D-fructose is dissolved in water by placing 10 mg of 3-deoxy-D-fructose in a very small sample vial. To this is added 250 ul of water, and this is mixed to dissolve the 3-deoxy-D-fructose. This stock solution is used for each reaction according to Table 5. In each case, 20 ul of the 3-deoxy-D-fructose solution is added first to a vial along with a mini stir bar. The remaining reagents are added in the order shown in Table 5 (left to right) and mixed by stirring on a stirplate. Each vial is capped and heated to 60° C. with stirring. After the reaction time, the vial contents are cooled and analyzed for 2,5-bis(hydroxymethyl)furan by HPLC analysis. Conversion of 3-deoxy-D-fructose into 2,5-bis(hydroxymethyl)furan is observed.

TABLE 5

Dehydration of 3-deoxy-D-fructose to form 2,5-bis(hydroxymethyl)furan

| # | Ac$_2$O (ul) | Acetic (ul) | HBr/HOAc (ul) | H$_2$O (ul) | Acid (ul) | Time (h) |
|---|---|---|---|---|---|---|
| 44 | — | 365 | 375 | — | — | 4 |
| 45 | — | — | 740 | — | — | 4 |
| 46 | 405 | 299 | — | — | H2SO$_4$, 36 | 4 |
| 47 | 365 | — | 375 | — | — | 4 |
| 48 | 364 | 263 | 113 | — | — | 4 |
| 49 | — | — | 675 | 65 | — | 4 |
| 50 | — | 337 | 338 | 65 | — | 4 |
| 51 | — | — | — | — | TFA, 740 | 4 |
| 52 | | | | 683 | TFA, 57 | 1 |
| 53 | | | | 700 | H$_2$SO$_4$, 40 | 1 |
| 54 | | | | 655 | HBr, 85 | 1 |
| 55 | | | | 641 | HI, 99 | 1 |

Example 56: Oxidation of 5-hydroxymethyl-2-furoic acid into furandicarboxylic acid 5-hydroxymethyl-2-furoic acid (2.5 g), acetic acid (30 ml), cobalt acetate (0.083 g), sodium bromide (0.071 g), and manganese acetate (0.084 g) are mixed in a batch reactor and placed under an excess of oxygen at 800 psig with vigorous mixing for 1 hour at 180° C. LC analysis of the total reaction mixture shows conversion of 5-hydroxymethyl-2-furoic acid to furandicarboxylic acid.

Example 57: Oxidation of 5-formal-2-furoic acid into furandicarboxylic acid 5-formyl-2-furoic acid (2.5 g), acetic acid (30 ml), cobalt acetate (0.083 g), sodium bromide (0.071 g), and manganese acetate (0.084 g) are mixed in a batch reactor and placed under an excess of oxygen at 800 psig with vigorous mixing for 1 hour at 180° C.

LC analysis of the total reaction mixture shows conversion of 5-formyl-2-furoic acid to furandicarboxylic acid.

Example 58: Oxidation of 2,5-bis(hydroxymethyl)furan into furandicarboxylic acid 2,5-bis(hydroxymethyl)furan (2.5 g), acetic acid (30 ml), cobalt acetate (0.083 g), sodium bromide (0.071 g), and manganese acetate (0.084 g) are mixed in a batch reactor and placed under an excess of oxygen at 800 psig with vigorous mixing for 1 hour at 180° C. LC analysis of the total reaction mixture shows conversion of 2,5-bis(hydroxymethyl)furan to furandicarboxylic acid.

Example 59: Oxidation of Fructose into D-lyxo-5-hexosulose

Fructose (100 g) and yeast extract (10 g) are mixed in 1 L of deionized water, and this medium is divided amongst several shake flasks. Each flask containing medium is inoculated with a culture of *Gluconobacter oxydans*, and incubated at 32° C. for 8 hours in a shaker with good agitation for medium aeration. During the fermentation, fructose is converted to D-lyxo-5-hexosulose.

Examples 60-71: Dehydration of D-lyxo-5-hexosulose into 2,5-diformylfuran

D-lyxo-5-hexosulose is dissolved in water by placing 10 mg of D-lyxo-5-hexosulose in a very small sample vial. To this is added 250 ul of water, and this is mixed to dissolve the D-lyxo-5-hexosulose. This stock solution is used for each reaction according to Table 6. In each case, 20 ul of the D-lyxo-5-hexosulose solution is added first to a vial along with a mini stir bar. The remaining reagents are added in the order shown in Table 6 (left to right) and mixed by stirring on a stirplate. Each vial is capped and heated to 60° C. with stirring. After the reaction time, the vial contents are cooled and analyzed for 2,5-bis(hydroxymethyl)furan by HPLC analysis. Conversion of D-lyxo-5-hexosulose into 2,5-diformylfuran is observed.

TABLE 6

Dehydration of D-lyxo-5-hexosulose to form 2,5-diformylfuran

| # | Ac₂O (ul) | Acetic (ul) | HBr/HOAc (ul) | H₂O (ul) | Acid (ul) | Time (h) |
|---|---|---|---|---|---|---|
| 60 | — | 365 | 375 | — | — | 4 |
| 61 | — | — | 740 | — | — | 4 |
| 62 | 405 | 299 | — | — | H₂SO₄, 36 | 4 |
| 63 | 365 | — | 375 | — | — | 4 |
| 64 | 364 | 263 | 113 | — | — | 4 |
| 65 | — | — | 675 | 65 | — | 4 |
| 66 | — | 337 | 338 | 65 | — | 4 |
| 67 | — | — | — | — | TFA, 740 | 4 |
| 68 | | | | 683 | TFA, 57 | 1 |
| 69 | | | | 700 | H₂SO₄, 40 | 1 |
| 70 | | | | 655 | HBr, 85 | 1 |
| 71 | | | | 641 | HI, 99 | 1 |

Example 72: Oxidation of 2,5-diformylfuran into furandicarboxylic acid 2,5-diformylfuran (2.5 g), acetic acid (30 ml), cobalt acetate (0.083 g), sodium bromide (0.071 g), and manganese acetate (0.084 g) are mixed in a batch reactor and placed under an excess of oxygen at 800 psig with vigorous mixing for 1 hour at 180° C. LC analysis of the total reaction mixture shows conversion of 2,5-diformylfuran to furandicarboxylic acid.

The invention claimed is:

1. A method of preparing 5-hydroxymethyl-2-furoic acid, the method comprising the steps of:
    (a) oxidizing glucose to provide gluconic acid by contacting the glucose with at least one enzyme to form the gluconic acid, wherein the at least one enzyme comprises at least one of a glucose oxidase and a glucose dehydrogenase;
    (b) dehydrating gluconic acid to provide 2-keto-3-deoxygluconic acid by contacting the gluconic acid with at least one enzyme to form the 2-keto-3-deoxygluconic acid, wherein the at least one enzyme comprises at least one of a galactonate dehydratase having the classification E.C. 4.2.1.6, an altronate dehydratase having the classification E.C. 4.2.1.7, a mannonate dehydratase having the classification E.C. 4.2.1.8, a dihydroxyacid dehydratase having the classification E.C. 4.2.1.9, a gluconate dehydratase having the classification E.C. 4.2.1.39, a glucarate dehydratase having the classification E.C. 4.2.1.40, a galactarate dehydratase having the classification E.C. 4.2.1.42, a D-fuconate dehydratase having the classification E.C. 4.2.1.67, a L-fuconate dehydratase having the classification E.C. 4.2.1.68, a xylonate dehydratase having the classification E.C. 4.2.1.82, a gluconate/galactonate dehydratase having the classification E.C. 4.2.1.140, and an L-galactonate dehydratase having the classification E.C. 4.2.1.146; and
    (c) dehydrating 2-keto-3-deoxygluconic acid to provide 5-hydroxymethyl-2-furoic acid.

2. The method of claim 1, wherein the glucose of step (a) is oxidized by a microbe to produce gluconic acid.

3. The method of claim 2, wherein the microbe is a *Pseudomonas* spp., an *Acetobacter* spp., a *Zymomonas* spp., a *Gluconobacter* spp., an *Azospirillum* spp., an *Aspergillus* spp., a *Penicillium* spp., a *Gliocladium* spp., a *Scopulariopsis* spp., a *Gonatobotrys* spp., an *Endomycopsis* spp., an *Aureobasidium* spp., a *Tricholoma* spp., or a *Gluconacetobacter* spp.

4. The method of claim 2, wherein the microbe is *Pseudomonas ovalis, Pseudomonas savastanoi, Acetobacter methanolicus, Zymomonas mobilis, Acetobacter diazotrophicus, Gluconobacter oxydans, Gluconobacter suboxydans, Azospirillum brasiliense, Aspergillus niger, Penicillium funiculosum, Penicillium glaucum, Penicillium variabile, Penicillium amagasakiense, Aureobasidium pullulans, Tricholoma robustum, Pseudomonas fluorescens,*

*Gluconobacter cerinus, Gluconacetobacter diazotrophicus, Acetobacter aceti, Acetobacter pasteurianus, Acetobacter tropicalis*, or *Gluconacetobacter xylinus*.

5. The method of claim 2, wherein the microbe is *Aspergillus niger*.

6. The method of claim 1, wherein the at least one enzyme of step (b) comprises at least one of a gluconate dehydratase and a dihydroxyacid dehydratase.

7. The method of claim 1, wherein the 2-keto-3-deoxygluconic acid of step (c) undergoes acid catalyzed dehydration by contacting the 2-keto-3-deoxygluconic acid with an acid to provide 5-hydroxymethyl-2-furoic acid.

8. The method of claim 7, wherein the acid comprises at least one of: acetic acid, sulphuric acid, trifluoroacetic acid, hydrobromic acid, hydrochloric acid, and hydroiodic acid.

9. The method of claim 1, wherein the 2-keto-3-deoxygluconic acid in step (c) is subjected to acid catalyzed dehydration by contacting the 2-keto-3-deoxygluconic acid with an acid and heated to a temperature in the range of 10° C. to 200° C. for a period of time of 5 minutes to 10 hours to provide 5-hydroxymethyl-2-furoic acid.

10. The method of claim 9, wherein the acid comprises at least one of: acetic acid, sulphuric acid, trifluoroacetic acid, hydrobromic acid, hydrochloric acid, hydroiodic acid.

11. The method of claim 1, wherein the at least one enzyme of step (a) comprises a glucose oxidase.

12. The method of claim 11, wherein the glucose of step (a) is oxidized by a microbe to produce gluconic acid, wherein the microbe is selected from the group consisting of *Aspergillus* spp., *Penicillium* spp., *Gliocladium* spp., *Scopulariopsis* spp., *Gonatobotrys* spp., *Endomycopsis* spp., *Aureobasidium* spp., and *Tricholoma* spp.

13. The method of claim 12, wherein the microbe is selected from the group consisting of *Aspergillus niger, Penicillium funiculosum, Penicillium glaucum, Penicillium variabile, Penicillium amagasakiense, Aureobasidium pullulans, Tricholoma robustum*, and *Pseudomonas fluorescens*.

14. The method of claim 1, wherein the at least one enzyme of step (a) comprises a glucose dehydrogenase.

15. The method of claim 14, wherein the glucose of step (a) is oxidized by a microbe to produce gluconic acid, wherein the microbe is selected from the group consisting of *Pseudomonas* spp., *Acetobacter* spp., *Zymomonas* spp., *Gluconobacter* spp., *Azospirillum* spp., and *Gluconacetobacter* spp.

16. The method of claim 15, wherein the microbe is selected from the group consisting of *Pseudomonas* spp., *Zymomonas* spp., and *Gluconobacter* spp.

* * * * *